United States Patent
Young et al.

[11] Patent Number: 5,549,544
[45] Date of Patent: Aug. 27, 1996

[54] APPARATUS FOR ULTRASONIC THERAPEUTIC TREATMENT

[75] Inventors: Michael J. R. Young, South Devon; Brian R. D. P. Bradnock, Herts, both of United Kingdom

[73] Assignee: Orthosonics Ltd., Ashburton, United Kingdom

[21] Appl. No.: 165,312

[22] Filed: Dec. 10, 1993

Related U.S. Application Data

[63] Continuation-in-part of PCT/GB93/00374, Feb. 25, 1993.

[30] Foreign Application Priority Data

Feb. 25, 1992 [GB] United Kingdom ............ 9204021

[51] Int. Cl.$^6$ .................................................. A61B 17/22
[52] U.S. Cl. ............................................................. 601/2
[58] Field of Search .......................... 128/660.03; 601/2, 601/46, 80; 604/22

[56] References Cited

U.S. PATENT DOCUMENTS

| | | | |
|---|---|---|---|
| 4,040,414 | 8/1977 | Suroff | 601/2 |
| 4,169,984 | 10/1979 | Parisi | 601/2 X |
| 4,176,454 | 12/1979 | Hatter et al. | 601/2 |
| 4,236,510 | 12/1980 | Hatter et al. | 601/2 |
| 4,823,775 | 4/1989 | Rindt | 601/2 X |

OTHER PUBLICATIONS

Wells, P. N. T. "Biomedical Ultrasonics", Academic Press London 1977, see pp. 53–58.

*Primary Examiner*—Francis Jaworski
*Attorney, Agent, or Firm*—Hopgood, Calimafde, Kalil & Judlowe

[57] ABSTRACT

The apparatus comprises a piezoelectric vibrator adapted to generate ultrasonic energy which is transmitted through an output section 1 to a plastics head 6. The shape of the head 6 may be varied to suit whichever part of a body on which it is to be used. The material and shape of the head 6 is chosen to allow accurate control of frequency and amplitude of the ultrasonic energy. The preferred ultrasonic frequency is in the range of 20–120 kHz.

23 Claims, 5 Drawing Sheets

APPARATUS FOR ULTRASONIC THERAPEUTIC TREATMENT

RELATED CASE

This application is a continuation-in-part of pending PCT/GB93/00374, filed Feb. 25, 1993.

BACKGROUND OF THE INVENTION

The present invention relates to a medical appliance for ultrasonic therapeutic treatment and/or other operation upon living body tissue.

The application of ultrasound in diagnostic scanning techniques and therapeutic treatment of specific medical conditions has been widely reported in the technical literature over the last 20 to 30 years. However, we have found no relevant reference to the use of frequencies in the range 30 to 100 kHz. The reported applications of therapeutic ultrasound relate almost exclusively to use of frequencies in the MHz band. This stems from the concept that therapeutic treatment using ultrasonic energy should be directed accurately to a well defined region of tissue and that this is best achieved with a finely focused beam, which in turn dictates the use of high frequencies. Similar arguments apply to the selection of frequencies for ultrasonic imaging applications. For example, the characteristic wavelength corresponding to a 3 MHz transmission through soft tissue is about 0.5 mm; but at 40 kHz, the wavelength would be approximately 37.5 mm.

Furthermore, it is known that the attenuation of ultrasonic waves increases with increasing frequency. The general effect of high frequency transmission is to produce relatively high energy absorption rates close to the entry surface, and for the effect to fall off with increasing depth. It might therefore be concluded that, for a given power input, there is a greater likelihood of potentially harmful side effects in tissue near the surface than for a corresponding low-frequency input when treating deep tissue injuries. This consideration becomes very important since in order to transmit enough energy to the required region, the risk of excessive absorption in surface layers may become unreasonably high when applying therapeutic ultrasound in the MHz band. For this reason, energy levels are limited by the requirement that power input should not exceed 3 watts/cm.

By selecting an operating frequency band in the range 30–130 kHz, a good wave penetration through deep muscle tissue is ensured and frequencies which are known to result in high attenuation in bone tissue are avoided.

Experience with this form of energy reveals a need to effect treatment in regions of the body which naturally inhibit access, particularly the hands and feet. In such cases, the use of a specially shaped therapy head may greatly facilitate the treatment of an injured joint. It is recognized that under such circumstances repetitive cyclic movement of the treatment head over the skin surface may be difficult and that the need to avoid the establishment of standing waves must therefore be satisfied by an alternative technique.

BRIEF STATEMENT OF THE INVENTION

It is an object of the present invention to address the problem of probe access while at the same time choosing an operating frequency which optimizes the relationship between wave penetration, treatment intensity and minimum risk of tissue damage.

According to one aspect of the present invention, there is provided an apparatus to treat muscular injuries below a body surface or to diagnose bone fractures, wherein the device comprises piezoelectric means to generate ultrasonic energy at a frequency in the range 20 to 120 kHz, an application head adapted to be applied closely to the body surface, and means to transfer said ultrasonic energy to the head means and thereby into the body.

The frequency range employed permits significantly higher energy dosage to deep-seated injuries without causing damage to surface tissue, as might be the case using more conventional high-frequency radiation.

According to another aspect of the invention, there are provided methods by which low-frequency vibrations are introduced through a molded plastic head permitting effective coupling to irregularly shaped surfaces and ensuring even energy distribution throughout the targeted volume of tissue.

The head may be machined or molded from a range of dense polymers including acetal, polypropylene and polycarbonate. These and similar materials all permit the transmission of low amplitude ultrasound in the frequency range 30 to 100 kHz, with very low energy absorption. The head is machined from plastics material which is chosen because its specific impedance (W) closely matches that of human soft tissue; generally, the head should have a wave impedance in the range of 1 to 1.2 times the wave impedance of human soft tissue. As an example, acetal may be used, in which case applicable figures are:

$$W_{acetal}=1.86\times10^6 \text{ kg m}^{-2}\text{sec}^{-1};$$

$$W_{soft\ tissue}=1.65\times10^6 \text{ kg m}^{-2}\text{sec}^{-1}.$$

This allows good coupling using virtually any fluid which excludes air from the head/tissue interface. It must be noted that this approach could not be used for radiation in the MHz band since absorption in the head material would be very high at those frequencies.

Clinical trials using this technique have so far proved that the treatment is effective in rapidly reducing pain levels related to conditions such as ankle sprains, anterior knee pain, lower back pain, neck and wrist sprains, and muscle spasm such as may be related to spasticity.

According to another aspect of the invention, there is provided a method for the application of low-frequency vibrations to an injured limb in order to provide a simple screening test for suspected fractures.

The presence of a hairline fracture would normally be detected by radiography, but if a high proportion of x-ray examinations prove negative, there is a strong argument for conducting a simple preliminary examination to identify those cases presenting definable symptoms. When a wave of ultrasound is transmitted through bone tissue containing a fine crack, the wave is partially reflected at the interface between the two sections of bone, due to the mechanical discontinuity in the transmission medium. Some energy is however absorbed at the site of the injury, causing a local transient sensation of pain which provides an initial indication of a fracture. It should be emphasized that this preliminary indication may result from a routine therapeutic treatment of an injury and not a specific intention to test for a fracture.

DETAILED DESCRIPTION OF THE INVENTION

Embodiments of the invention will now be described more particularly, by way of example, and with reference to the accompanying drawings, in which:

FIG. 3 is a transducer and head assembly of an appliance as in FIG. 2 but with a housing, shown in longitudinal section for compliant suspension of said assembly within the housing;

FIG. 4 is a view limited to the applicator-end region of the appliance, to show an applicator head of modified contour;

FIG. 5 is a view similar to FIG. 4, to show an applicator head with another modified contour;

FIG. 6 is a view similar to FIG. 3, to show a further modified applicator-head contour;

FIG. 7 is a view similar to FIGS. 4 and 5, to show still another modified contour;

Figure 1:
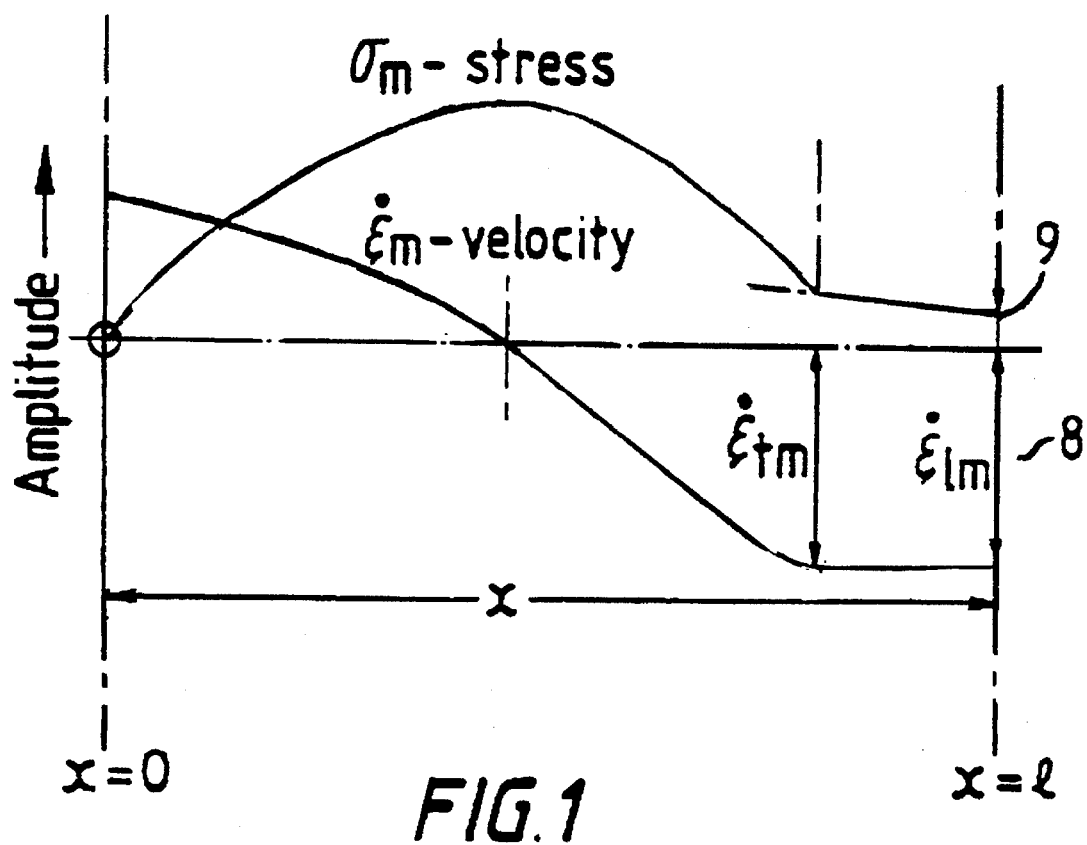
FIG. 1 is a graphical representation of the velocity and stress distributed along the axis of a transducer and head of the invention, with indication of the travelling wave amplitude in the head.
Figure 2:
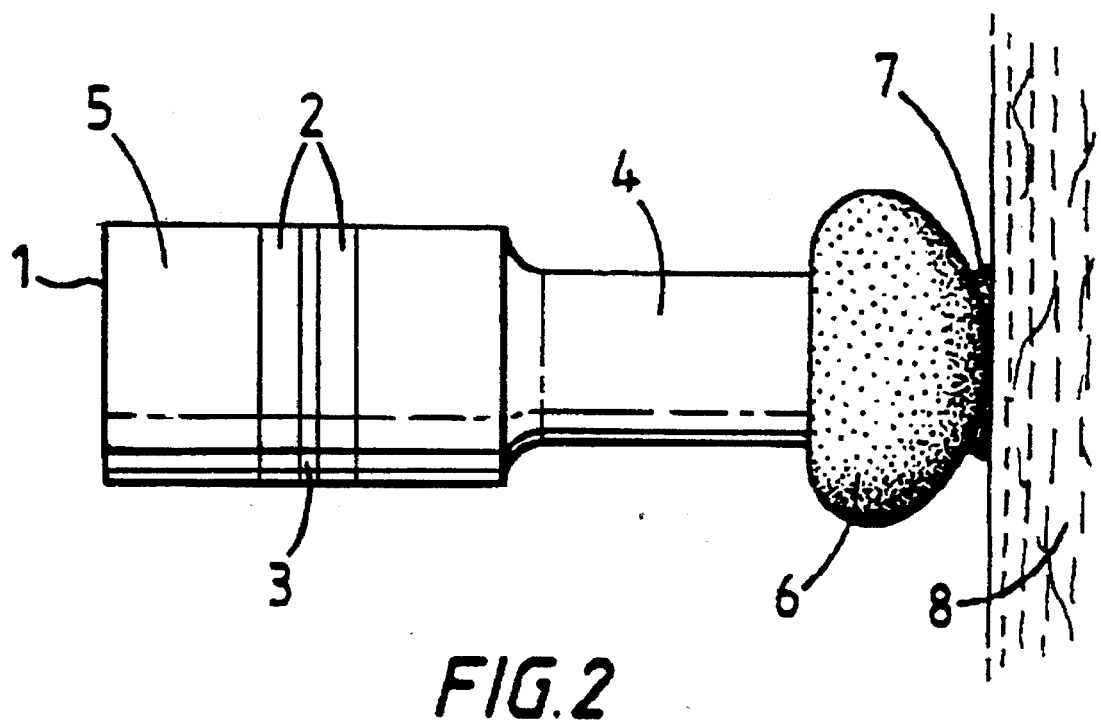
FIG. 2 is a schematic view of an appliance comprising a piezoelectric transducer and head assembly, to the same scale of overall length as the dimension x of FIG. 1.
Figure 3:
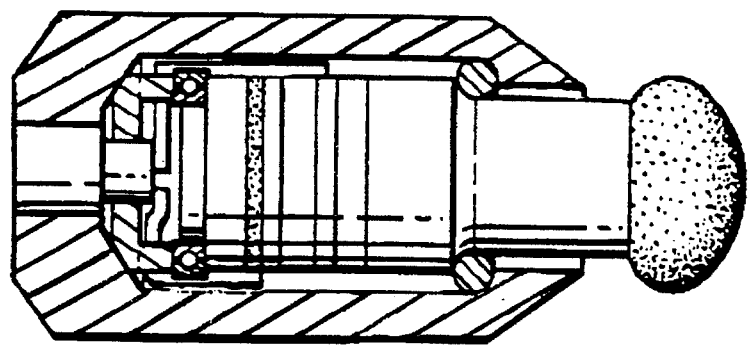
FIGS. 3 to 7 are further views as in FIG. 2, to show alternative head members for use in apparatus of the present invention, namely.
Figure 4:
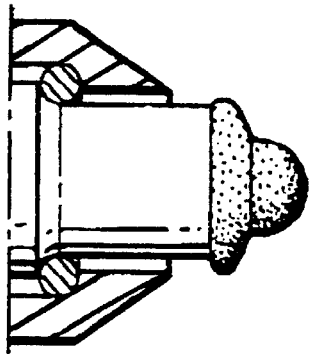
Figure 5:
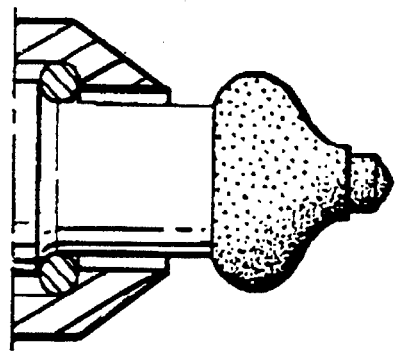
Figure 6:
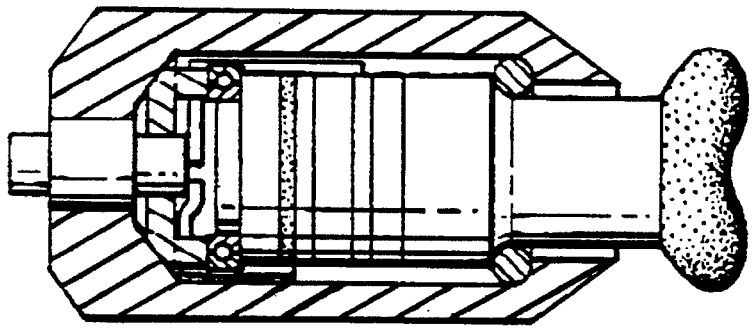
Figure 7:
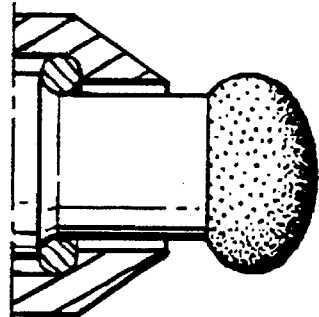

Referring now to the drawings, FIG. 2 shows a vibrator in the form of a PZT sandwich transducer incorporating a backplate 5, PZT ceramic rings 2 (piezoelectric transducer means), an electrode 3 and a stepped output section 4. This vibrator transmits waves at a predetermined frequency through a shaped plastic head 6 into tissue 8 via a coupling medium 7. FIG. 1 shows the waveform in the system. A standing pressure wave is established in the transducer with output amplitude at 9, and this is transmitted through a shaped therapy head 6, emerging as a travelling wave of amplitude $\xi_{LM}$. The velocity and pressure-wave amplitudes (stress) in the plastic head are seen to be relatively constant under loaded conditions; they therefore represent the travelling-wave amplitude for energy transmitted into the patient. This condition is established due to reflection at the transducer/head interface and almost complete transmission at the head/tissue interface. The shape of the head may be varied at least according to the examples given in FIGS. 3 to 7. This characteristic reflects the particular properties of the plastics chosen for the head construction which allows accurate control of frequency and amplitude. For given transducer dimensions, the shape and size of the head can be varied between wide limits while maintaining a controlled output power. As shown in FIGS. 2, 3, 7 and 9, the treatment head (6) may provide a substantially hemispherical convex body-application surface wherein the outer diameter of the treatment head exceeds the diameter of the output section 4 to which the treatment head is coupled, and wherein the center of the body-application surface is on the central axis of the output section. Remaining shape of the treatment head adopts a rounding of proximal peripheral edges which would otherwise be sharply defined in a more strictly geometric hemispherical shape.

Figure 8:
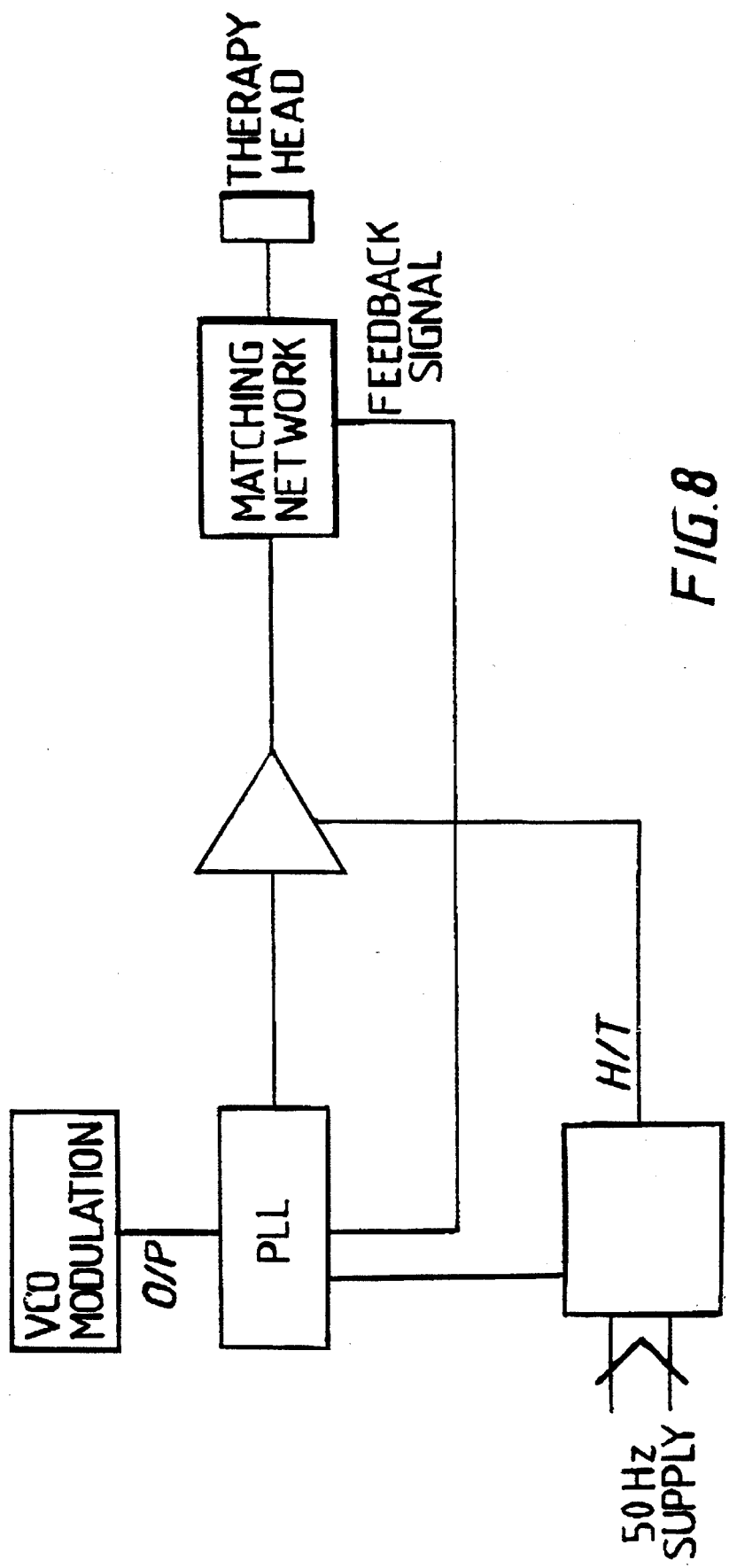
FIG. 8 is a block diagram schematically showing an electrical drive system for the transducer and head configurations of FIGS. 2 to 7.

In operation, the energy transmitted to the subject tissue must not result in standing waves since this might cause excessive local absorption. This would normally be avoided by moving the head over the tissue surface during treatment; however, when treating the hand or other inaccessible area, such movement may be inhibited by the head shape and an alternative method must be used. The broad-band transmission characteristic of the head permits the use of frequency modulation derived from the system shown in the drawings (FIG. 8).

Figure 10:
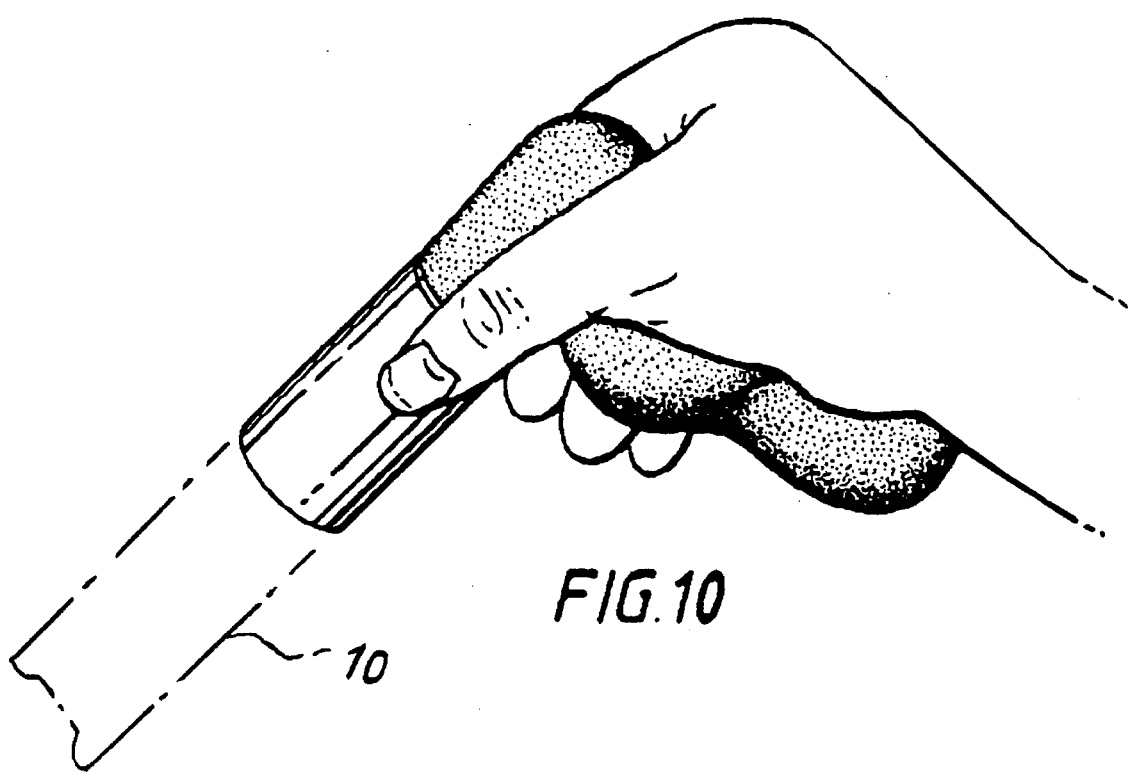
FIGS. 10 and 11 are perspective views of an embodiment adapted for use on an injured hand.
Figure 11:
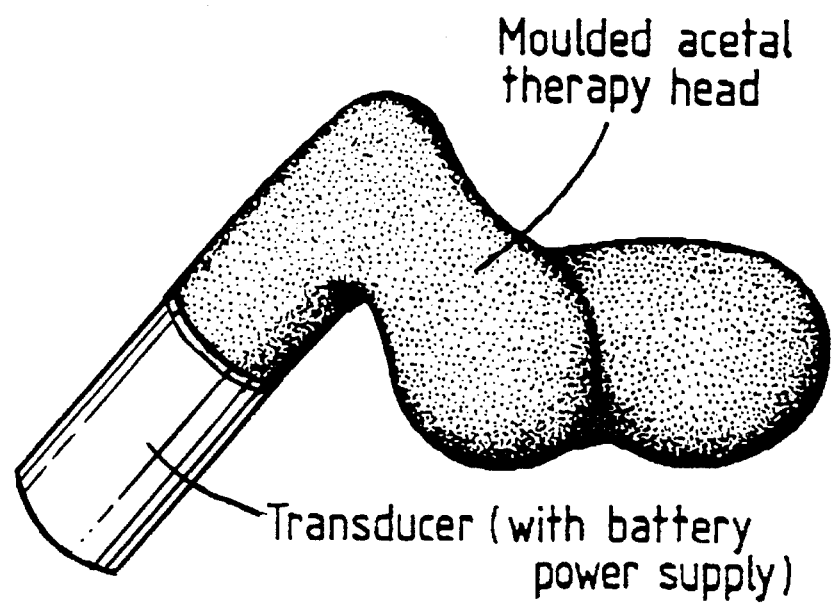

A further advantage which derives from the use of a plastics-moldable head is the ability to employ a shaped head designed to give maximum contact in locations with difficult access, e.g., hands and feet. For example, in severe cases of rheumatoid arthritis, the head could be molded to form a hand grip which when held by the patient would permit general treatment of the hand joints simultaneously. This is shown in FIGS. 10 and 11. When the power input is supplied by battery means or some other transportable source, the transducer may be located within the stem (suggested at 10) of a walking stick or cane, the grip of which comprises the head.

This invention offers an improved method and means for the therapeutic treatment of deep-seated soft-tissue injuries by ensuring that adequate power is safely transmitted to the affected region. It offers a novel means of treating irregularly shaped areas, using molded or machined heads that allow good transmission of energy without the need to traverse the surface.

According to the invention, there is provided an apparatus which offers a major benefit in the technique available to monitor the treatment power delivered to a patient.

It is known that the intensity, I, of transmitted ultrasound is related to displacement amplitude $\xi$, by the expression:

$$I = \frac{1}{2\rho c \omega^2 \xi^2} .$$

where $\rho$ is the head-material density, c is the phase velocity and $\omega$ is the angular frequency, defined as $2\pi f$.

Figure 9:
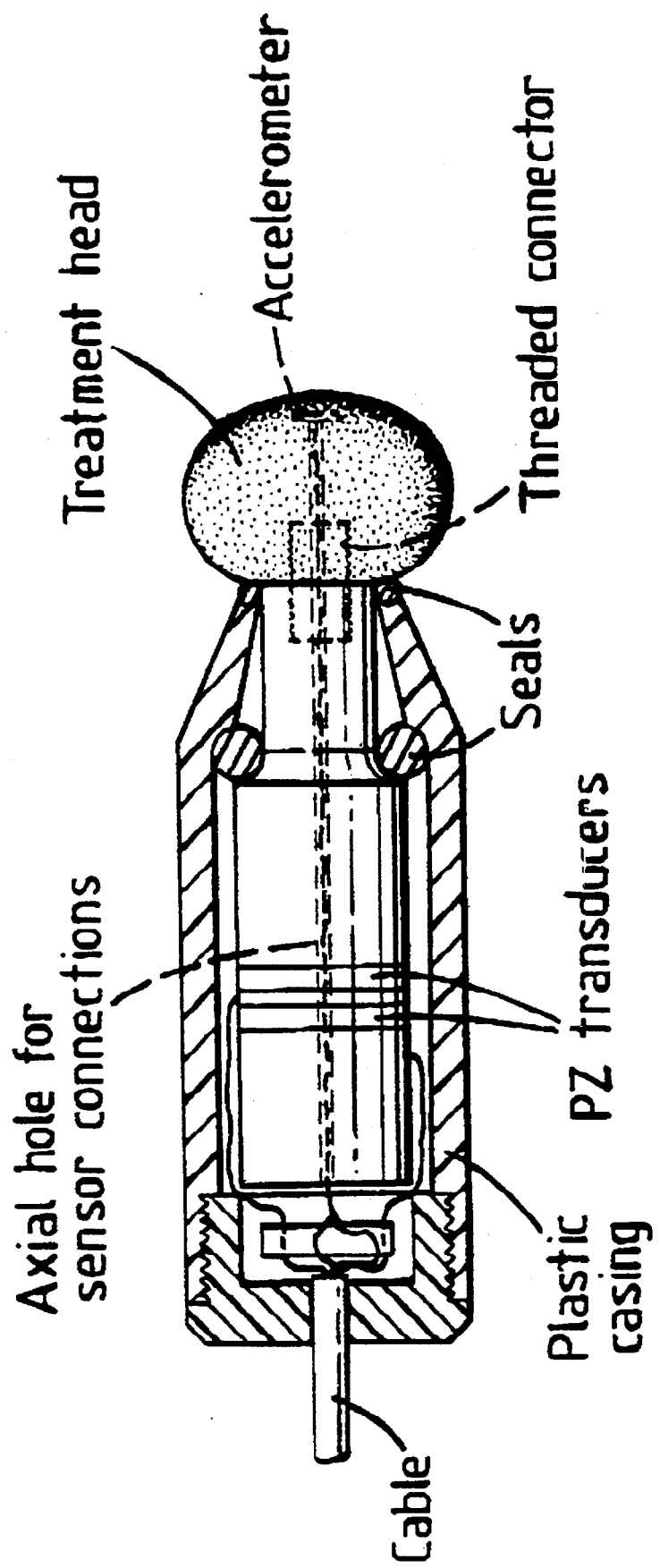
FIG. 9 shows an apparatus embodying the invention and incorporating an accelerometer.

Since $\rho c$ is the wave impedance of the head material which by design substantially matches that of the treated tissue, then I–$\xi$. If we monitor the displacement amplitude within the treatment head, it is a relatively simple matter to obtain a linear signal, proportional to displacement amplitude and intensity, using a differentiating amplifier. This method offers much greater reliability than the current technique which depends on monitoring the electrical signal to the transducer. Any variation in the transducer performance would therefore cause a power measuring error. FIG. 9 shows a head with a displacement sensor or accelerometer incorporated. This enables the displacement amplitude of vibrations transmitted to the patient to be determined. The measurements may be transmitted to indicating means for the user to control the power input. The output of the displacement sensor may alternatively be used to control directly the power input.

What is claimed is:

1. An apparatus to treat muscular injuries below a body surface, comprising piezoelectric transducer means including an elongate output member for distally supplying ultrasonic energy in the range of 20 to 120 kHz and on a longitudinal axis via said output member, a head means connected to and carried distally by said output member and having a smoothly continuous convex body-treatment surface that is axially spaced distally beyond the location of connection to said output member, said body-treatment surface having a predetermined effective treatment area, said head means having a wave impedance in the range of 1 to 1.2 times the wave impedance of soft human tissue, and the body-treatment surface of said head means being adapted to be applied directly to and to be manipulated continuously over a body area to be treated wherein the body area to be treated is greater than the effective treatment area of said head means.

2. An apparatus as claimed in claim 1, in which the frequency is in the range of 30 to 100 kHz.

3. An apparatus as claimed in claim 1, in which the frquency is in the region of 40 kHz.

4. An apparatus as claimed in claim 1, in which means are provided in said head means to determine displacement amplitude at the treatment surface of the said head means.

5. An apparatus as claimed in claim 4, in which said means to determine displacement amplitude is an accelerometer producing an electrical output signal, and means including a differentiating amplifier to process said output signal to a signal proportional to displacement amplitude.

6. An apparatus as claimed in claim 1, in which said body-treatment surface is generally hemispherical.

7. An apparatus as claimed in claim 1, in which said piezoelectric transducer means comprises on said axis a piezoelectric sandwich interposed between a backplate and said output member.

8. An apparatus as claimed in claim 1, in which said head means is of acetal material, and the wave impedance of said body-applicator head is substantially $1.86 \times 10^6$ kg m$^{-2}$ sec$^{-1}$.

9. An apparatus as claimed in claim 1, in which said transducer means comprises on said axis a piezoelectric sandwich interposed between a backplate and an output section which distally includes said output member, and a tubular housing surrounding and in radially spaced relation to said piezoelectric transducer means at two axially spaced locations of compliant housing support of said transducer means, said axially spaced locations being at opposite axial offsets from said piezoelectric sandwich.

10. A method of treating muscular injuries below a living-body surface comprising applying to said surface a means of transmitting ultrasonic energy via an elongate output member to a distal-end location and at a frequency in the range of 20 to 120 kHz, said application being via an intermediate body of plastics material interposed between said output member and the living-body surface, wherein the plastics material is selected from the group consisting of acetal, polypropylene and polycarbonate, and wherein the body of plastics material has a smoothly continuous convex surface adapted for application to the living-body surface, and wherein the body of plastics material provides the only path of ultrasonic-energy coupling of the output member to the living-body surface.

11. The method of non-invasively supplying ultrasonic energy to living body tissue beneath a selected region of skin, which comprises selecting a body applicator of a material having a wave impedance that is within a range of up to 1.2 times the wave impedance of human soft tissue, wherein the selected body applicator has a smoothly continuous body-contact surface, and applying ultrasonic energy in the frequency range of 20 to 120 kHz directly to the selected region of skin but only via said body applicator, with its body-contact surface in contact with the selected region of skin.

12. The method of claim 11, in which the ultrasonic energy is in the range of 30 to 100 kHz.

13. The method of claim 11, in which the ultrasonic frequency range is 40 kHz, plus or minus substantially 5 kHz.

14. An apparatus to treat muscular injuries below a living body surface, comprising piezoelectric transducer means including an elongate output member for distally applying ultrasonic energy in the range of 20 to 120 kHz and on a longitudinal axis via said output member, a head means of plastics material connected to and carried distally by said output member and having a smoothly continuous convex body-application surface that is shaped for close application to the body surface and is axially spaced distally beyond the location of connection to said output member, the plastics of said head means being of a material selected from the group consisting of: acetal, polypropylene and polycarbonate, whereby said head means is able to provide exclusive coupling of ultrasonic energy to the body surface.

15. An apparatus as claimed in claim 14, in which said head means is shaped for manually gripped accommodation within a hand.

16. An apparatus as claimed in claim 15, in which said head means forms a hand grip of a cane or walking stick having a stem, and said piezoelectric transducer means is accommodated within the stem of the cane or walking stick.

17. An apparatus as claimed in claim 14, in which the ultrasonic energy is at a frequency in the range of 40 kHz, plus or minus 5 kHz.

18. An apparatus as claimed in claim 14, in which said piezoelectric transducer means comprises on said axis a piezoelectric sandwich interposed between a backplate and said output member.

19. An apparatus to treat muscular injuries below a body surface, comprising piezoelectric transducer means including an elongate output member for distally supplying ultrasonic energy in the range of 20 to 120 kHz and on a longitudinal axis via said output member, a head means connected to and carried distally by said output member and having a smoothly continuous convex body-treatment surface that is axially spaced distally beyond the location of connection to said output member, said body-treatment surface having a predetermined effective treatment area, said head means having a wave impedance that is relatively close to the wave impedance of living body tissue and that is relatively remote from the wave impedance of said output member, and the body-treatment surface of said head means being adapted to be applied directly to and to be manipulated continuously over a body area to be treated wherein the body area to be treated is greater than the effective treatment area of said head means.

20. An apparatus as claimed in claim 19 in which the wave impedance of said head means is in the range of 1 to 1.2 times the wave impedance of human soft tissue.

21. An apparatus as claimed in claim 19, in which the wave impedance of said head means is substantially $1.86 \times 10^6$ kg m$^{-2}$ sec$^{-1}$.

22. The method of non-invasively supplying ultrasonic energy to living body tissue beneath a selected region of skin, which comprises selecting a body applicator of a material having a wave impedance that is substantially matched to the wave impedance of living tissue, wherein the body applicator has a smoothly continuous convex surface configured for skin contact at the selected region, and applying axially directed ultrasonic energy in the frequency range of 20 to 120 kHz directly to the body applicator at a location which is axially offset from the smoothly continuous convex surface of the body applicator, the application of ultrasonic energy to the living body being solely via the body applicator.

23. The method of claim 22, in which the convex body-applicator surface is generally circular and has a span which is a fraction of a wavelength at the frequency of application to the living body.

* * * * *